US009723985B2

(12) United States Patent
Ono et al.

(10) Patent No.: US 9,723,985 B2
(45) Date of Patent: Aug. 8, 2017

(54) VITAL SIGN TELEMETER

(75) Inventors: Kohei Ono, Tokyo (JP); Fumiyuki Matsumura, Tokyo (JP); Koji Ishino, Tokyo (JP); Shinya Suzuki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1741 days.

(21) Appl. No.: 11/006,539

(22) Filed: Dec. 8, 2004

(65) Prior Publication Data

US 2005/0171444 A1    Aug. 4, 2005

(30) Foreign Application Priority Data

Dec. 8, 2003 (JP) ................................ 2003-409552

(51) Int. Cl.
*A61B 5/022* (2006.01)
*A61B 5/00* (2006.01)
*A61B 5/083* (2006.01)
*A61B 5/1455* (2006.01)

(52) U.S. Cl.
CPC ............ *A61B 5/0002* (2013.01); *A61B 5/022* (2013.01); *A61B 5/0836* (2013.01); *A61B 5/1455* (2013.01)

(58) Field of Classification Search
CPC . A61B 5/022; A61B 5/02208; A61B 5/02225; A61B 5/02233; A61B 5/02241; A61B 5/0225; A61B 5/02255; A61B 5/0235; A61B 5/02422; A61B 5/025; A61B 5/0002
USPC ................ 600/490–503, 483–486, 481, 488, 600/322–324, 326, 310, 300, 301
See application file for complete search history.

(56) References Cited

U.S. PATENT DOCUMENTS

| | | | | |
|---|---|---|---|---|
| 3,659,592 A | * | 5/1972 | Natkanski | A61B 5/02233 600/499 |
| 3,752,147 A | * | 8/1973 | Castro et al. | 600/499 |
| 4,548,249 A | * | 10/1985 | Slaughterbeck | 206/363 |
| 4,566,463 A | * | 1/1986 | Taniguchi et al. | 600/495 |
| 4,625,277 A | * | 11/1986 | Pearce | A61B 5/022 128/923 |
| 4,677,984 A | * | 7/1987 | Sramek | 600/494 |
| 4,729,381 A | * | 3/1988 | Harada et al. | 600/484 |

(Continued)

FOREIGN PATENT DOCUMENTS

| | | |
|---|---|---|
| JP | 61-33640 A | 2/1986 |
| JP | 63-216543 A | 9/1988 |

(Continued)

OTHER PUBLICATIONS

Japanese Office Action dated Dec. 16, 2008.

*Primary Examiner* — Navin Natnithithadha
(74) *Attorney, Agent, or Firm* — Sughrue Mion, PLLC

(57) ABSTRACT

A first detector is provided with a cuff adapted to be placed on an upper arm of a subject to detect noninvasive blood pressure of the subject. At least one second detector is adapted to be placed on a part of the subject to detect at least one vital sign of the subject. A single main body is detachably provided on the cuff while being connected with the first detector and the at least one second detector. A display is provided on the main body and operable to display the non-invasive blood pressure and the at least one vital sign as measurement data. A transmitter is provided in the main body and operable to transmit the measurement data to a receiver placed in a remote location.

7 Claims, 20 Drawing Sheets

(56) References Cited

U.S. PATENT DOCUMENTS

| | | | |
|---|---|---|---|
| 4,745,915 A * | 5/1988 | Enright et al. | 128/853 |
| 4,776,339 A | 10/1988 | Schreiber | |
| 4,780,824 A * | 10/1988 | Niwa et al. | 600/513 |
| 4,873,987 A * | 10/1989 | Djordjevich et al. | 600/485 |
| 4,889,132 A * | 12/1989 | Hutcheson | A61B 5/02208 600/481 |
| 4,898,180 A * | 2/1990 | Farrelly et al. | 600/494 |
| 4,974,597 A * | 12/1990 | Walloch | 600/493 |
| 5,050,613 A * | 9/1991 | Newman et al. | 600/490 |
| 5,199,438 A * | 4/1993 | Pearlman | 600/483 |
| 5,215,096 A * | 6/1993 | Zapf et al. | 600/495 |
| 5,238,001 A * | 8/1993 | Gallant et al. | 600/513 |
| 5,309,908 A * | 5/1994 | Friedman et al. | 600/322 |
| 5,485,848 A * | 1/1996 | Jackson et al. | 600/485 |
| 5,586,552 A * | 12/1996 | Sakai | 600/493 |
| 5,620,001 A * | 4/1997 | Byrd | A61B 5/02233 600/490 |
| 5,651,368 A * | 7/1997 | Napolitano et al. | 600/490 |
| 5,669,390 A * | 9/1997 | McCormick et al. | 600/499 |
| 5,687,732 A | 11/1997 | Inagaki et al. | |
| 5,752,913 A * | 5/1998 | Oka | 600/300 |
| 5,830,149 A * | 11/1998 | Oka et al. | 600/500 |
| 5,836,887 A * | 11/1998 | Oka et al. | 600/494 |
| 5,895,359 A * | 4/1999 | Peel, III | 600/494 |
| 6,120,459 A * | 9/2000 | Nitzan et al. | 600/493 |
| 6,241,680 B1 * | 6/2001 | Miwa | 600/494 |
| 6,241,682 B1 * | 6/2001 | Ochiai et al. | 600/510 |
| 6,251,080 B1 * | 6/2001 | Henkin et al. | 600/490 |
| 6,344,025 B1 * | 2/2002 | Inagaki et al. | 600/490 |
| 6,379,310 B1 * | 4/2002 | Mori et al. | 600/490 |
| 6,471,087 B1 * | 10/2002 | Shusterman | 221/2 |
| 6,547,741 B2 * | 4/2003 | Mori et al. | 600/490 |
| 6,733,462 B1 * | 5/2004 | Frick et al. | 600/503 |
| 7,232,412 B2 * | 6/2007 | Shirasaki et al. | 600/490 |
| 2004/0064054 A1 * | 4/2004 | Clift | A61B 5/0205 600/483 |
| 2004/0147848 A1 * | 7/2004 | Shirasaki | A61B 5/02116 600/490 |

FOREIGN PATENT DOCUMENTS

| | | |
|---|---|---|
| JP | 3-31404 U | 3/1991 |
| JP | 3-85138 A | 4/1991 |
| JP | 8-107885 A | 4/1996 |
| JP | 8-126616 A | 5/1996 |
| JP | 9-322882 A | 12/1997 |
| JP | 10-302188 A | 11/1998 |
| JP | 2000-83912 A | 3/2000 |

\* cited by examiner

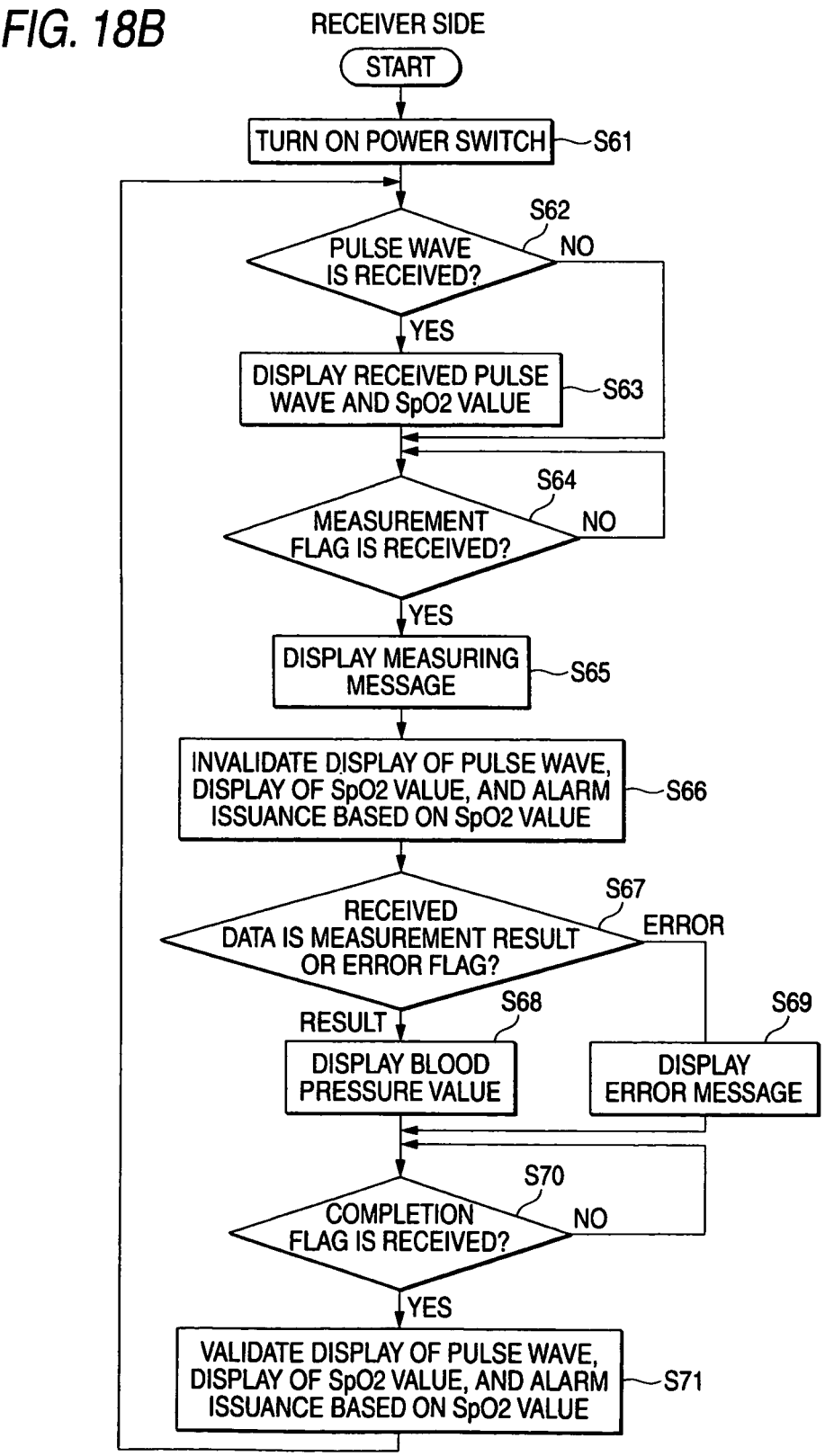

VITAL SIGN TELEMETER

BACKGROUND OF THE INVENTION

The present invention relates to a vital sign telemeter serving as patient monitor for respectively determining and monitoring vital signals (vital signs), such as an electrocardiograph, respiration, blood pressure, body temperature, and oxygen saturation (SpO2) in blood, of a patient in a serious condition in an ICU, CCU, or an emergency room, a patient undergoing an operation, or a patient being in an emergency transportation, or a patient whose condition can change suddenly.

Nowadays, a vital sign telemeter of this type must be capable of simultaneous measurement of a number of measurement items (parameters); and a vital sign telemeter which is configured to be able to measure electrocardiogram, a respiration curve, body temperature, oxygen saturation (SpO2) in blood, non-invasive blood pressure (NIBP), or the like, as the first parameters has been proposed and put into practice. Furthermore, as functional configurations for a vital sign telemeter of this kind, the following are important: being compact, lightweight, and easily attachable to a patient (living body); display of processing results of vital sign data is easily viewed so that conditions of a patient can be recognized; capable of being operated for a long time with stability; providing highly reliable data and alarm; convenient to handle and operate; and the like.

There is known a vital sign telemeter, which is configured so as to measure vital signals (vital signs) constituted of a number of parameters; e.g., an electrocardiogram, impedance respiration, oxygen saturation (SpO2) in blood, and non-invasive blood pressure (NIBP); to receive the signals, and to process and display the signals as required vital sign data, has a large configuration, and has complicated signal wiring of sensors for measurement of the respective parameters. Accordingly, difficulty is encountered when a patient walks while wearing such a vital sign telemeter attached to an upper arm thereof, which poses restrictions on the patients activities. Namely, the vital sign telemeter has a drawback of sacrificing the patient's QOL (quality of life).

Furthermore, as equipment for measurement of a single vital signal as found in a blood pressure monitor, there is known equipment in which a cuff for measurement of blood pressure and a device configured to process a measured vital signal, thereby displaying the vital signal, are integrated to be attached to an upper arm of a patient or the like. However, as described hitherto, there has been neither suggested nor embodied a vital sign telemeter in which a detector, a processor and a display for vital signals constituted of a number of parameters as required vital signals are integrated, and configured to be attached to an upper arm of a patient, or the like, to thus enable monitoring of the patient at the patient's side or from a remote site in an easy and convenient manner.

SUMMARY OF THE INVENTION

It is therefore an object of the invention to provide a vital sign telemeter capable of being attached onto an upper arm of a patient while integrating a detector, a processor and a display for plural kinds of vital signs including at least blood pressure into a single unit.

It is also an object of the invention to provide a vital sign telemeter capable of executing safety operation even when a single fault condition in connection with the blood pressure measurement (specifically defined by IEC 60601-2-30 Ed. 2.0:1999 (en)) is established.

It is also an object of the invention to provide a vital sign telemeter which is convenient in handling so as to reduce the burden on a patient caused by applying the vital sign telemeter even if the above requirements are satisfied.

In order to achieve the above objects, according to the invention, there is provided a vital sign telemeter, comprising:
a first detector, comprising a cuff adapted to be placed on an upper arm of a subject to detect non-invasive blood pressure of the subject;
at least one second detector, adapted to be placed on a part of the subject to detect at least one vital sign of the subject;
a single main body, detachably provided on the cuff while being connected with the first detector and the at least one second detector;
a display, provided on the main body and operable to display the non-invasive blood pressure and the at least one vital sign as measurement data; and
a transmitter, provided in the main body and operable to transmit the measurement data to a receiver placed in a remote location.

Preferably, at least one of the first detector and the at least one second detector is detachably connected to the main body.

Preferably, the at least one second detector includes at least one of: a plurality of electrodes, adapted to be attached on at least one of a chest and a limb of the subject to detect at least one of electrocardiogram and respiration of the subject; a sensor, adapted to be attached on a finger of the subject to detect oxygen saturation in blood of the subject; and a sensor, adapted to be attached on a face of the subject to detect a concentration of carbon dioxide in gas expired through nostrils of the subject.

With the above configuration, since the detectors for obtaining plural kinds of vital signs and the display for displaying the detected vital signs as the measurement data are integrated into the single main body attached on the cuff placed on the upper arm of the subject, it is convenient to handle so as to reduce burdens on the subject caused by applying the vital sign telemeter.

In addition, since the first detector and the at least one second detector are used as consumable components, it is advantageous that these consumable components can be replaced conveniently, and handling is easy.

Here, it is preferable that the display is so configured as to simultaneously display, as the measurement data, the noninvasive blood pressure, the oxygen saturation in blood, pulse rate, pulse wave, and an interval between periodic activation of the first detector.

Preferably, a face of the main body to be faced the upper arm is curved.

Preferably, a retainer detachably retains the main body on the cuff, and a cover sheet is provided on the cuff and configured to securely surround the main body retained on the cuff.

In this case, the maintenance of the main body can be facilitated by configuring the cuff and the main body detachably; and in that the patient's unusual feeling by applying the vital sign telemeter as medical equipment can be lessened by improving the fitting sense of the cuff.

Here, it is preferable that the retainer is disposed between the cuff and a face of the main body facing the upper arm so as to extend in a first direction which is perpendicular to a winding direction of the cuff; and a width of the retainer in a second direction which is perpendicular to the first direction is narrower than a width of the main body in the second direction.

In this case, since a gap is not allowed between the cuff and the arm, not only the cuff can be securely wound even around a thin arm, but also fitting feeling to the patient is enhanced; and since excess inflation of the cuff is eliminated, amplitude of a blood pressure signal is enlarged, whereby performance of blood pressure measurement can be enhanced.

Preferably, a first switch is adjacent to the display and adapted to be actuated to activate or deactivate the first detector; and a second switch is adjacent to the display and adapted to be actuated to determine an interval between periodic activation of the first detector.

Preferably, the transmitter transmits the measurement data in a wireless manner.

Preferably, a safety controller deflates the cuff when the first detector falls into a single fault condition which results in a failure in inflating operation of the cuff.

According to the invention, there is provided a telemeting method, comprising steps of:
  providing a first detector comprising a cuff adapted to be placed on an upper arm of a subject;
  providing at least one second detector adapted to be placed on a part of the subject;
  connecting the first detector and the at least one second detector to a single main body which is detachably provided on the cuff;
  detecting non-invasive blood pressure of the subject through the first detector;
  detecting at least one vital sign of the subject through the second detector;
  displaying the non-invasive blood pressure and the at least one vital sign on a display provided on the main body, as measurement data; and
  transmitting the measurement data to a receiver placed in a remote location.

According to the invention, there is also provided a telemeting system, comprising:
  a first detector, comprising a cuff adapted to be placed on an upper arm of a subject to detect non-invasive blood pressure of the subject;
  a second detector, adapted to be placed on a finger of the subject to detect oxygen saturation in blood of the subject;
  a single main body, detachably provided on the cuff while being connected with the first detector and the second detector;
  a receiver, placed in a remote location from the main body and provided with an indicator; and
  a transmitter, provided in the main body and operable to transmit the non-invasive blood pressure and the oxygen saturation in blood as measurement data to the receiver, wherein:
  the transmitter transmits information indicating that the measurement data for the oxygen saturation is unreliable at least while the first detector detects the non-invasive blood pressure, to the receiver; and
  the indicator indicates that the measurement data for the oxygen saturation received from the transmitter is unreliable when the receiver receives the information.

With the above configuration, since it is easily indicated that the SpO2 value obtained during the NIBP measurement is unreliable, the reliability of the vital sign telemeter can be enhanced.

BRIEF DESCRIPTION OF THE DRAWINGS

The above objects and advantages of the present invention will become more apparent by describing in detail preferred exemplary embodiments thereof with reference to the accompanying drawings, wherein:

FIGS. 18A and 18B are flowcharts showing a program for performing communication control executed between the vital sign telemeter and a receiver.

DETAILED DESCRIPTION OF THE INVENTION

Embodiments of the present invention will be described below in detail with reference to the accompanying drawings.

Figure 1:
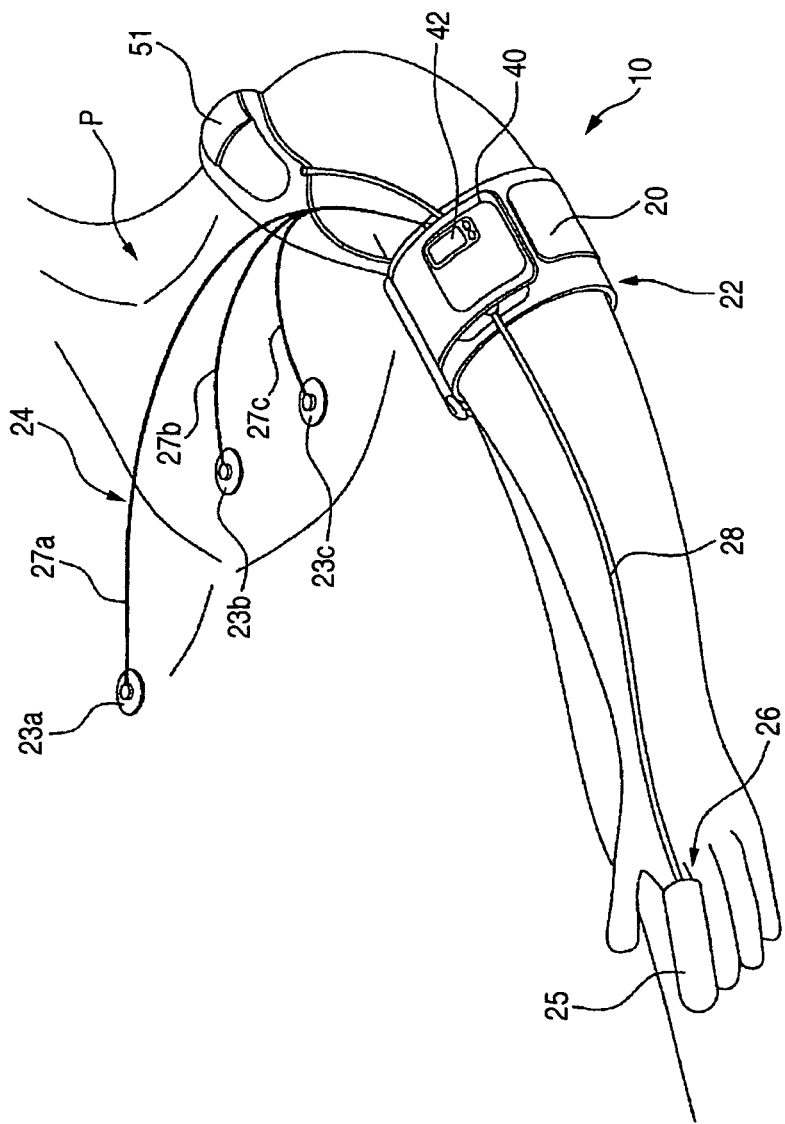
FIG. 1 is a perspective view of a vital sign telemeter according to a first embodiment of the invention, showing a state that the telemeter is attached onto a patients body.

FIG. 1 shows a vital sign telemeter 10 according to one embodiment of the invention comprises: a blood pressure detector 22 for detecting blood pressure by a cuff 20 placed around an upper arm of a patient P; an electrocardiogram and respiration detector 24 for detecting an electrocardiogram and respiration by attaching a plurality of electrodes 23a, 23b, 23c on a chest and/or a limb of the patient P; an SpO2 detector 26 for detecting oxygen saturation (SpO2) in blood by attaching a sensor probe 25 on a finger of the patient P; a main body 40 having a display 42 for processing and displaying vital signals detected and measured with use of the respective detector 22, 24, 26, and a transmitter (unillustrated) for transmitting the vital signals to a remote location in a wireless manner.

The main body 40 of the vital sign telemeter 10 is configured so that the main body 40 is detachably integrated with the cuff 20; and so that electrode lead wires 27a, 27b, 27c for use in connecting the main body 40 with the respective electrodes 23a, 23b, 23c of the electrocardiogram and respiration detector 24, and a sensor probe lead wire 28 for use in connecting the main body 40 with the sensor probe 25 of the SpO2 detector 26 are detachably connected to the main body 40. Meanwhile, in FIG. 1, the main body 40 integrated with the cuff 20 is provided with a retainer 51 for use of securely retaining the main body 40 on the shoulder of the patient P, as required.

Figure 2:
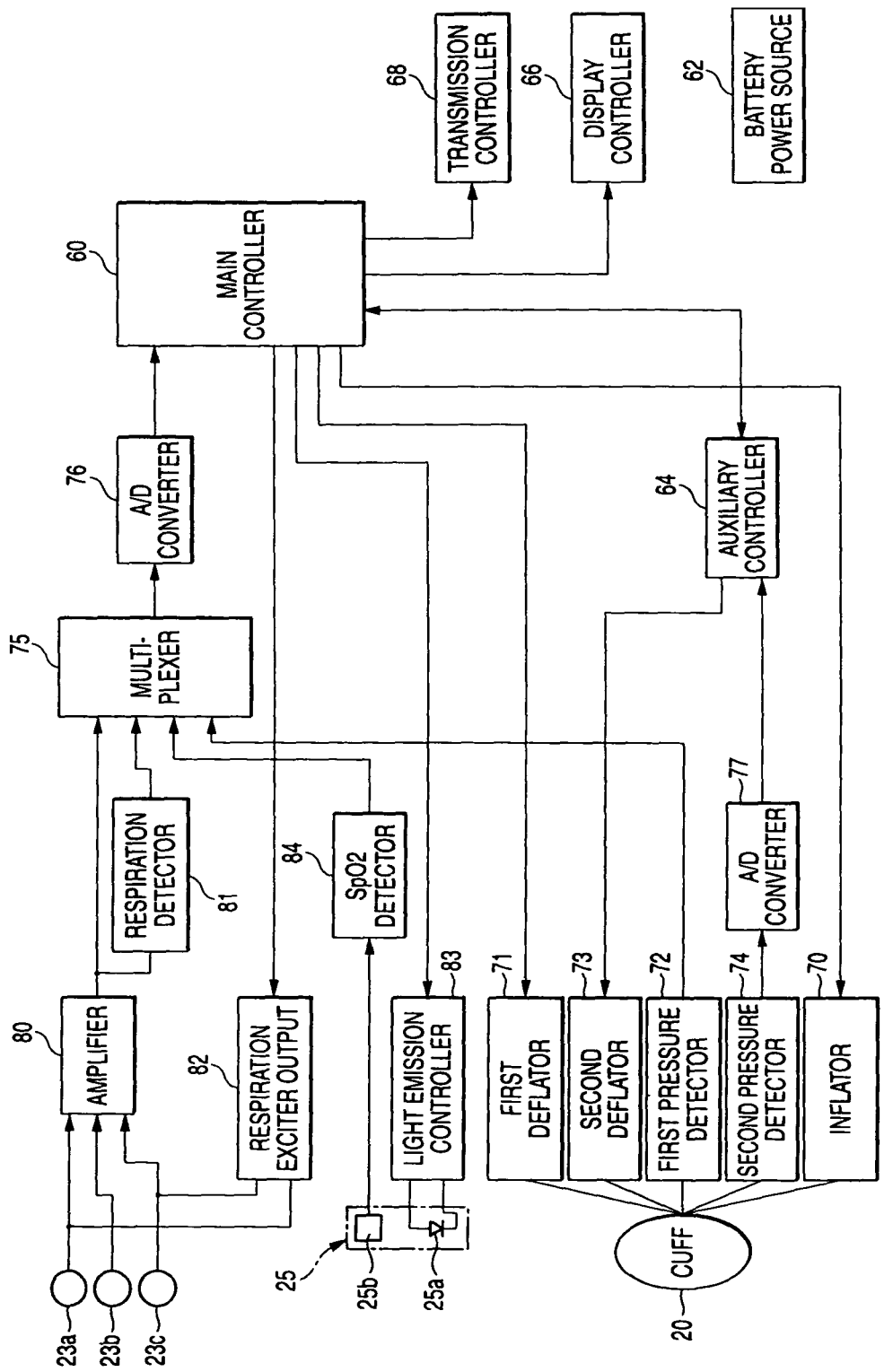
FIG. 2 is a block diagram showing the system configuration of the vital sign telemeter.

FIG. 2 shows a system configuration of the main body 40 of the vital sign telemeter 10. More specifically, reference numeral 60 denotes a main controller, 62 denotes a battery power source, and 64 denotes an auxiliary controller. The main controller 60 is connected to a display controller 66 serving as the display 42 and to a transmission controller 68 serving as the transmitter, respectively, and is also connected to the auxiliary controller 64. The display controller 66 and the transmission controller 68 are set to process vital signals detected by the detector 22, 24, 26 so as to display or transmit the vital signals.

In the vital sign telemeter 10, a inflator 70, a first deflator 71 and a first pressure detector 72, and a second deflator 73 and a second pressure detector 74 are respectively connected to the cuff 20 serving as the blood pressure detector. Herein, the inflator 70 and the first deflator 71 are controlled by the main controller 60, and blood pressure detected by the first pressure detector 72 is input to the main controller 60 by way of a multiplexer 75 and an A/D converter 76. The second deflator 73 is controlled by the auxiliary controller 64, and blood pressure detected by the second pressure detector 74 is input to the auxiliary controller 64 by way of an AND converter 77.

Vital signals detected by the respective electrodes 23a, 23b, 23c serving as the electrocardiogram and respiration detector 24 are input to the main controller 60 by way of an amplifier 80, a respiration detector 81, the multiplexer 75, and the A/D converter 76. The vital signals detected by the respective electrodes 23a, 23c are supplied with timing signals for detection of impedance respiration, by the main controller 60 by way of a respiration exciter output 82.

Furthermore, in a sensor 25 constituted of a light-emitting element 25a and a light-receiving element 25b serving as the SpO2 detector 26, the light-emitting element 25a is subject to light emission control by the main controller 60 by way of a light emission controller 83. A signal detected by the light-receiving element 25b is measured as oxygen saturation (SpO2) in blood by an SpO2 detector 84, and input into the main controller 60 by way of the multiplexer 75 and the A/D converter 76.

Figure 3:
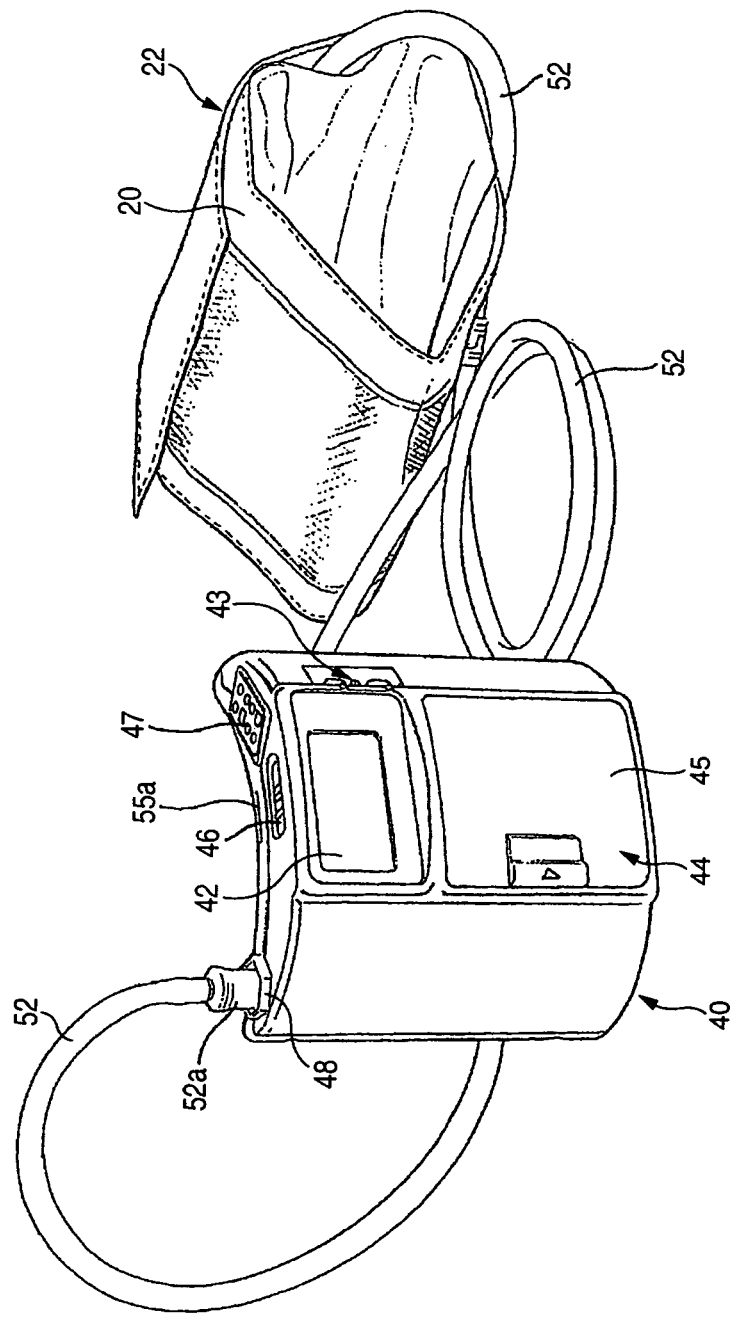
FIG. 3 is a perspective view of the vital sign telemeter showing a state that the telemeter is separated from a cuff.
Figure 4:
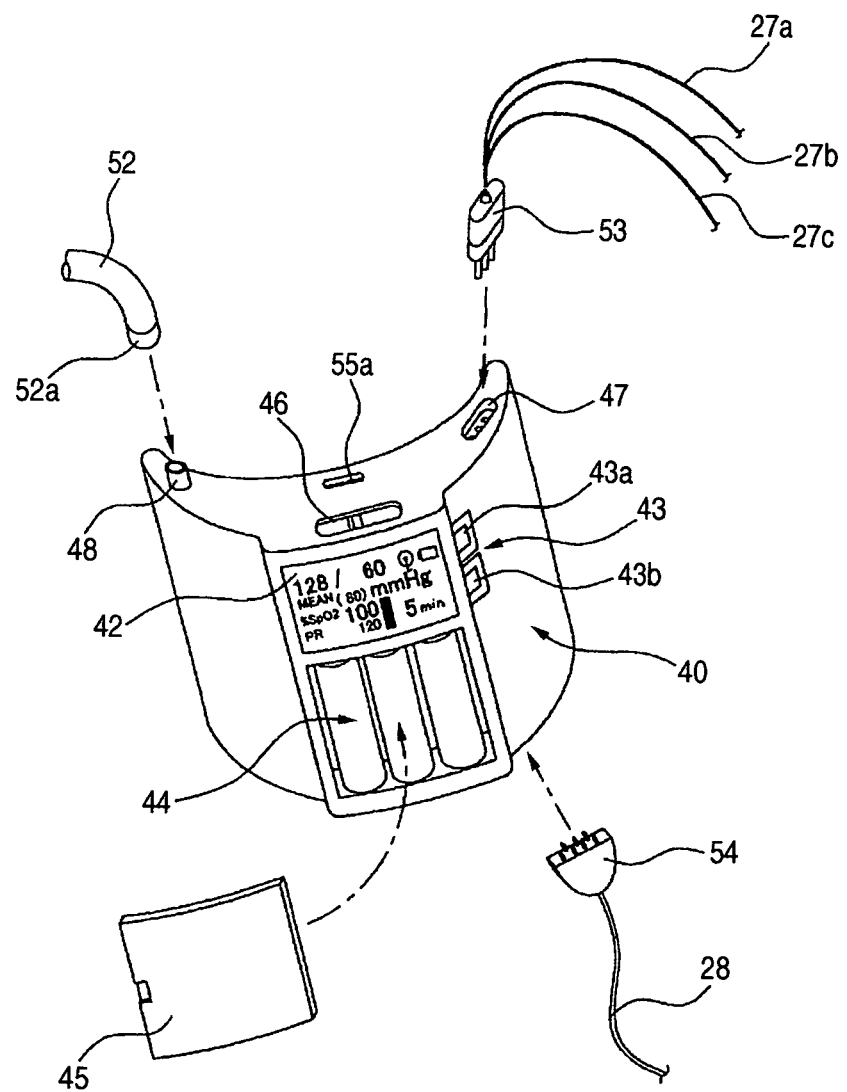
FIG. 4 is a top perspective view of the vital sign telemeter and connectors to be connected thereto.
Figure 5:
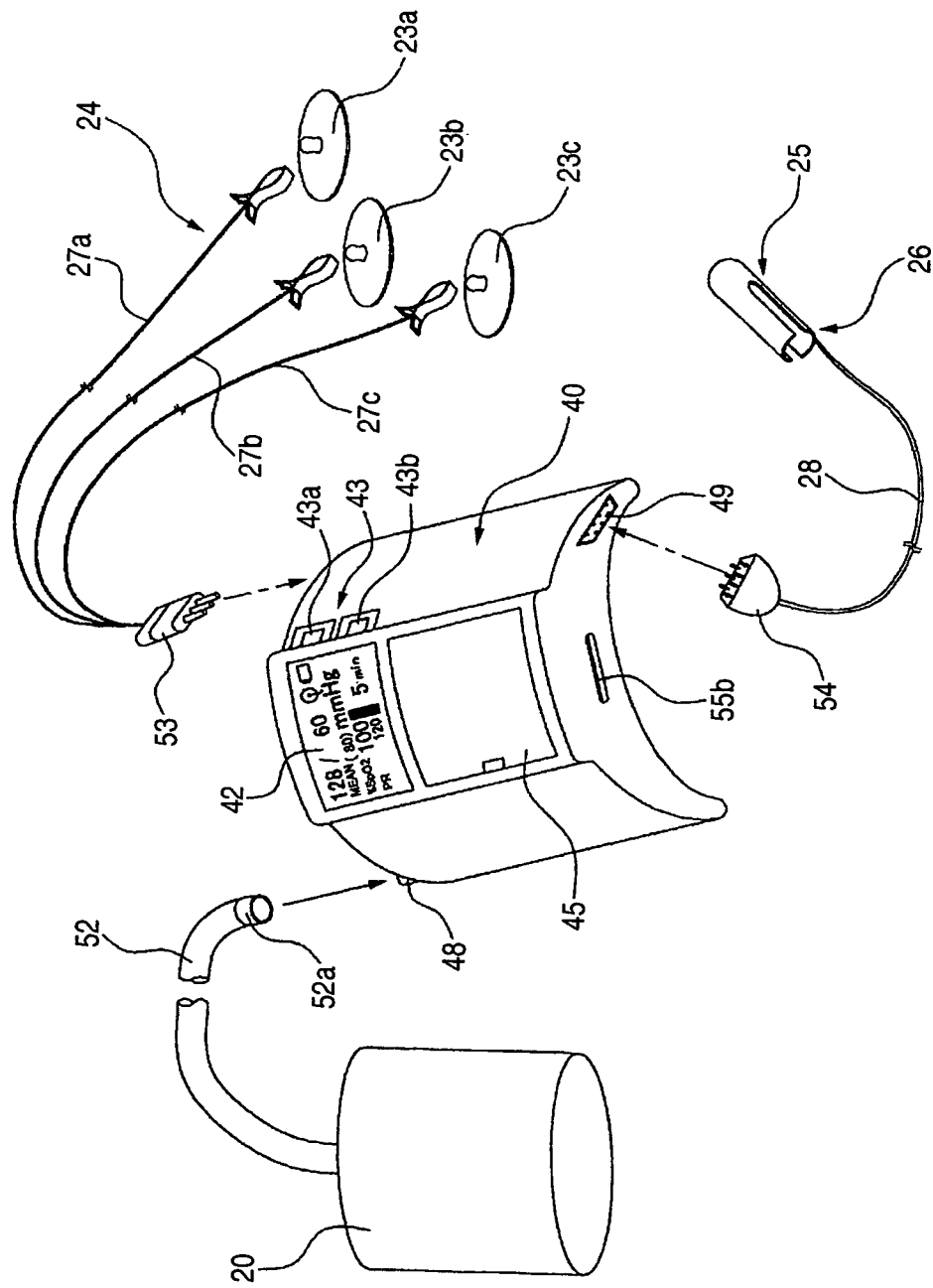
FIG. 5 is a bottom perspective view of the vital sign telemeter and detectors to be connected thereto.

FIG. 3 is a view showing, in a separated state, the cuff 20 and the main body 40 of the vital sign telemeter 10. Herein, as shown in FIGS. 3 to 5, the main body 40 has the display 42 at the upper center of the front face thereof, and a battery storage section 44 at the lower center of the front face. The back face of the main body 40 is formed into a curved shape so as to fit an upper arm of a patient during attachment. The display 42 comprises an LCD panel. In the vicinity of the display 42, there is provided an NIBP measurement adjuster 43 including a measurement start/stop switch 43a and a measurement interval setting switch 43b. A cover 45 is detachably provided on the battery storage section 44 (see FIG. 4).

On the top face of the main body 40, a power switch 46, a connector 47 for measurement of electrocardiogram and respiration, and a connector 48 for measurement of NIBP are provided. A connector 53 provided with electrode lead wires 27a, 27b, 27c for measurement of the electrocardiogram and respiration can be detachably connected to the connector 47, and a connector 52a provided with a cuff hose 52 can be detachably connected to the connector 48 (see FIGS. 4 and 5). A connector 49 for measurement of oxygen saturation (SpO2) in blood is provided on the bottom face of the main body 40. A connector 54 provided with a sensor probe lead wire 28 for measurement of SpO2 can be detachably connected to the connector 49 (see FIG. 5).

Furthermore, a slit 55a is provided on the top face of the main body 40, and a slit 55b is provided on the bottom face of the main body 40. The slits 55a, 55b are for engagement with a retainer 32, which will be described later, for use when the main body 40 is attached to the cuff 20 (see FIGS. 4 and 5).

Figure 6:
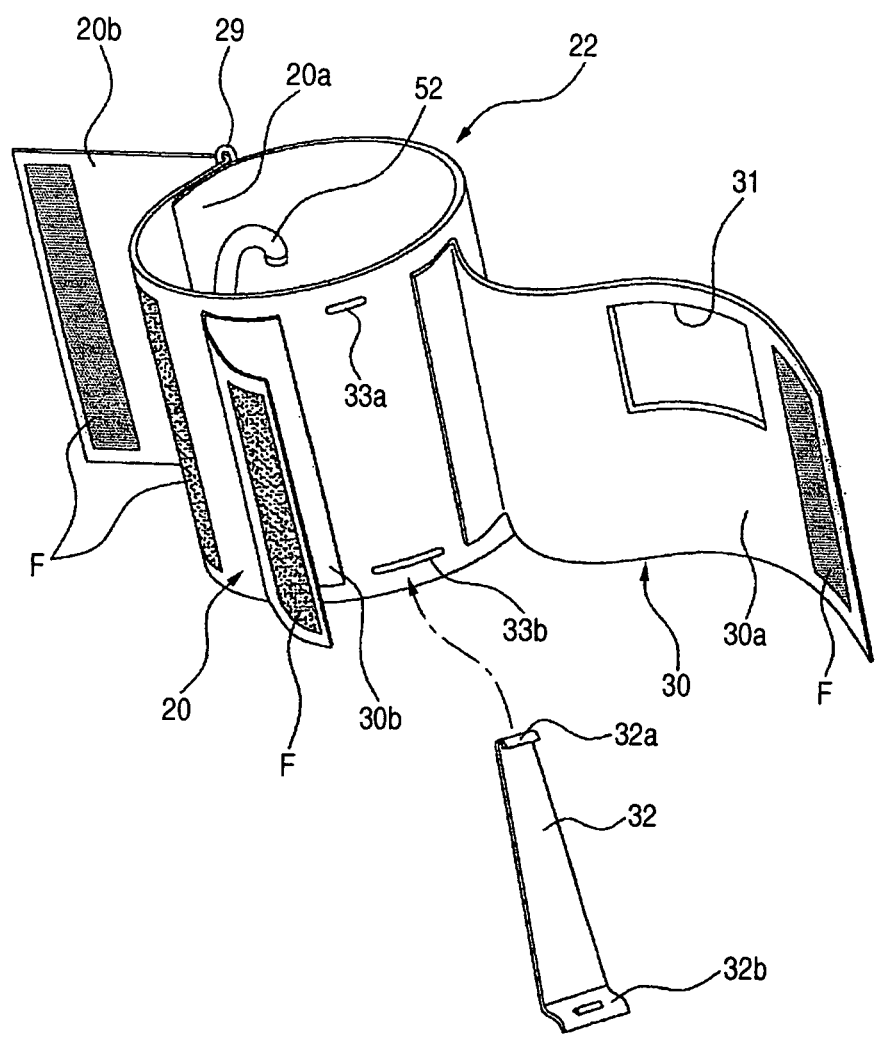
FIG. 6 is a perspective view of the cuff, showing a state before a retainer is attached.
Figure 7:
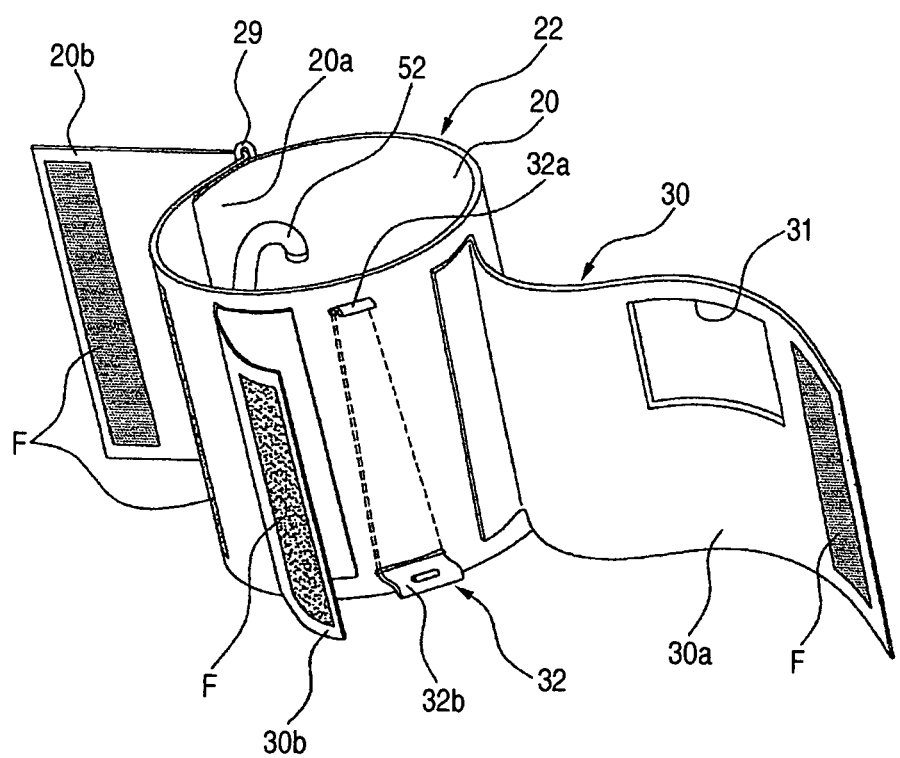
FIG. 7 is a perspective view of the cuff, showing a state after the retainer is attached.

As shown in FIGS. 6 and 7, the retainer 32 is attached to a portion of the cuff 20 placed around an upper arm of a patient, in order to retain the main body 40 of the vital sign telemeter 10 on the cuff 20. As shown in FIG. 6, slits 33a, 33b are provided on the cuff 20, and the retainer 32 having engagement sections 32a, 32b on both ends is attached to the cuff 20 through the slits 33a, 33b. As the result, attachment of the retainer 32 to the cuff 20 can be carried out in a convenient manner.

A sheet cover 30 for covering the main body 40 in an attached state is provided at a position corresponding to the position where the retainer 32 is provided. The sheet cover 30 comprises a cover body 30a with one end thereof being fixed on the cuff 20, and a fitting piece 30b with one end thereof being fixed to the cuff 20. On the cover body 30a, there is provided a window 31 for allowing visual check of the display 42 in a case where the main body 40 is covered. Hook-and-loop fasteners F are provided on the other end of the cover body 30a and that of the fitting piece 30b, whereby the cover body 30a and the fitting piece 30b can be joined to and separated from each other.

A size adjustment ring 29 is provided at one end 20a of the cuff 20. Accordingly, by passing the size adjustment ring 29 through the other end 20b of the cuff 20, a length of the cuff 20 placed around an upper arm of a patient can be adjusted as required. For this reason, another hook-and-loop fastener F for the purpose of fixedly connecting the other end 20b of the cuff 20 which has passed though the size adjustment ring 29 is provided on the inner face of the other end 20b of the cuff 20 as required.

Figure 8:
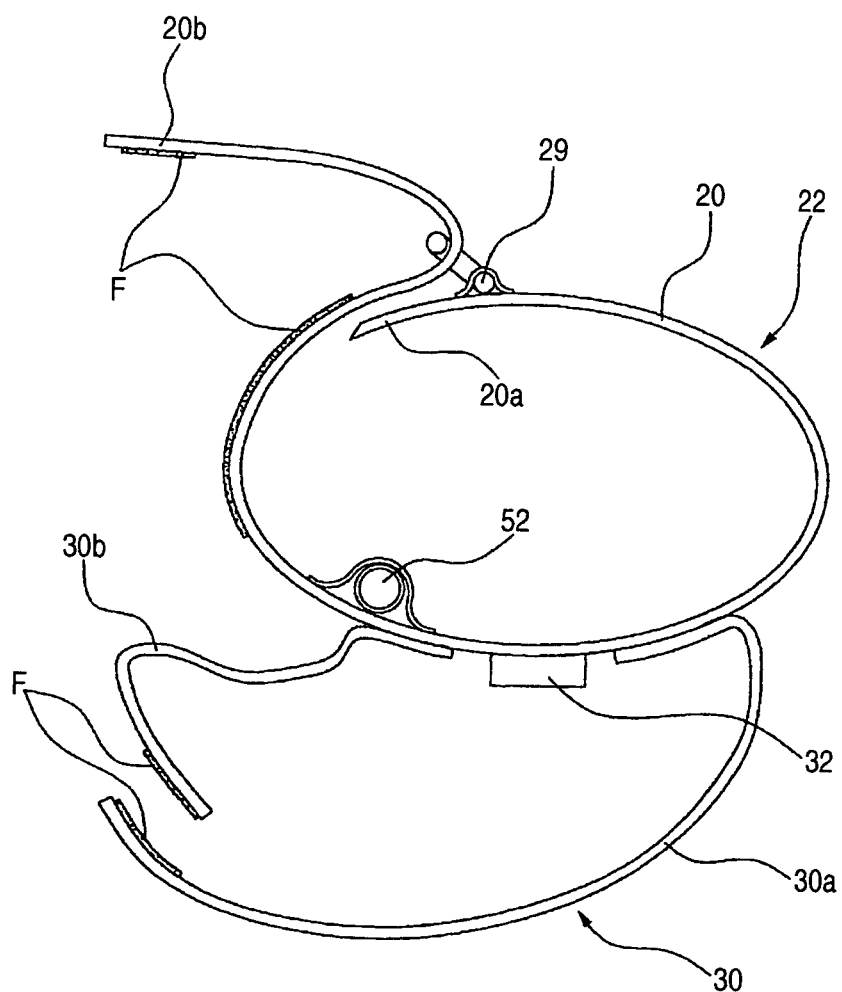
FIG. 8 is a plan view of the cuff shown in FIG. 7.

Accordingly, the cuff 20 configured as has been described can be attached to an upper arm of a patient by being formed into a ring-shape as shown in FIG. 8; and allows mounting of the main body 40 of the vital sign telemeter 10 by being provided with the retainer 32 and the sheet cover 30.

Figure 9:
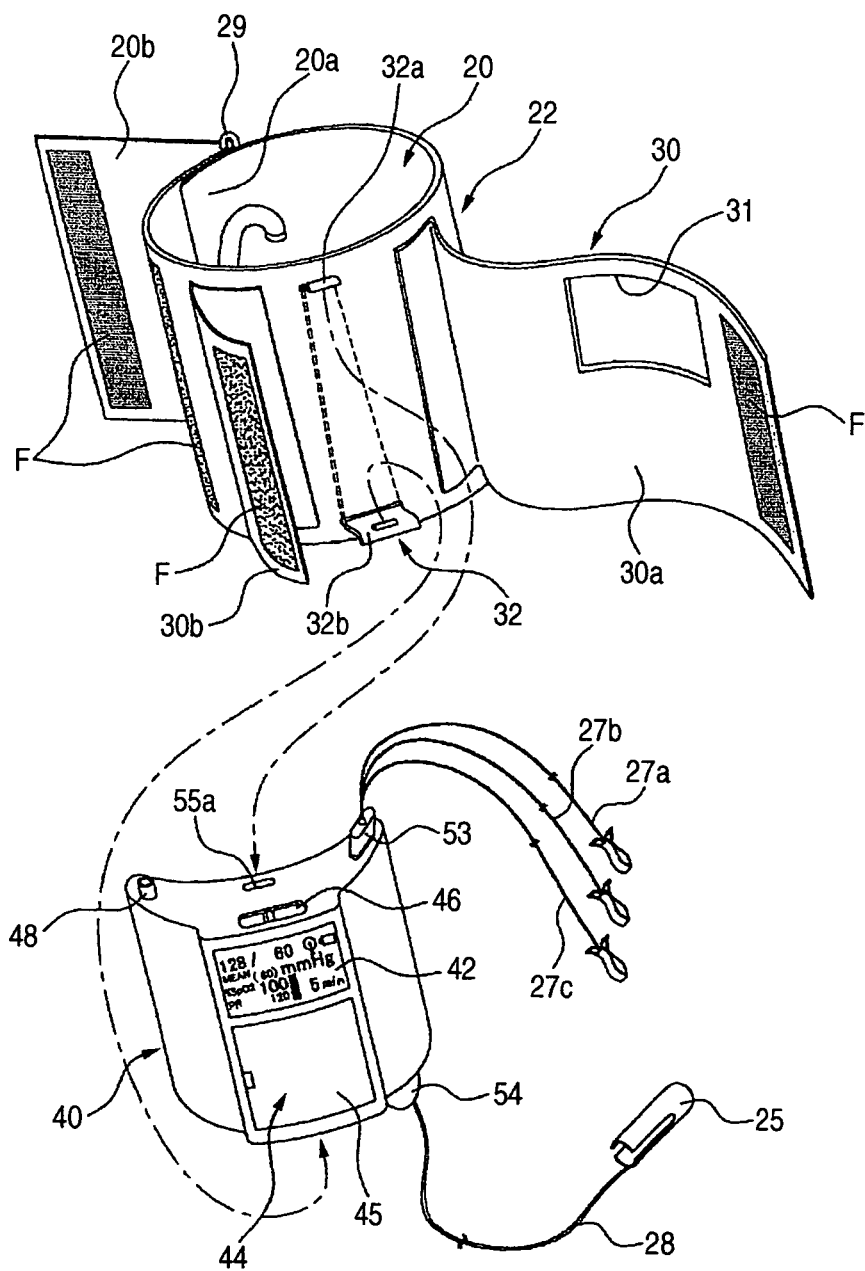
FIG. 9 is a perspective view of the vital sign telemeter and the cuff showing a state before the vital sign telemeter is attached on the cuff.
Figure 10:
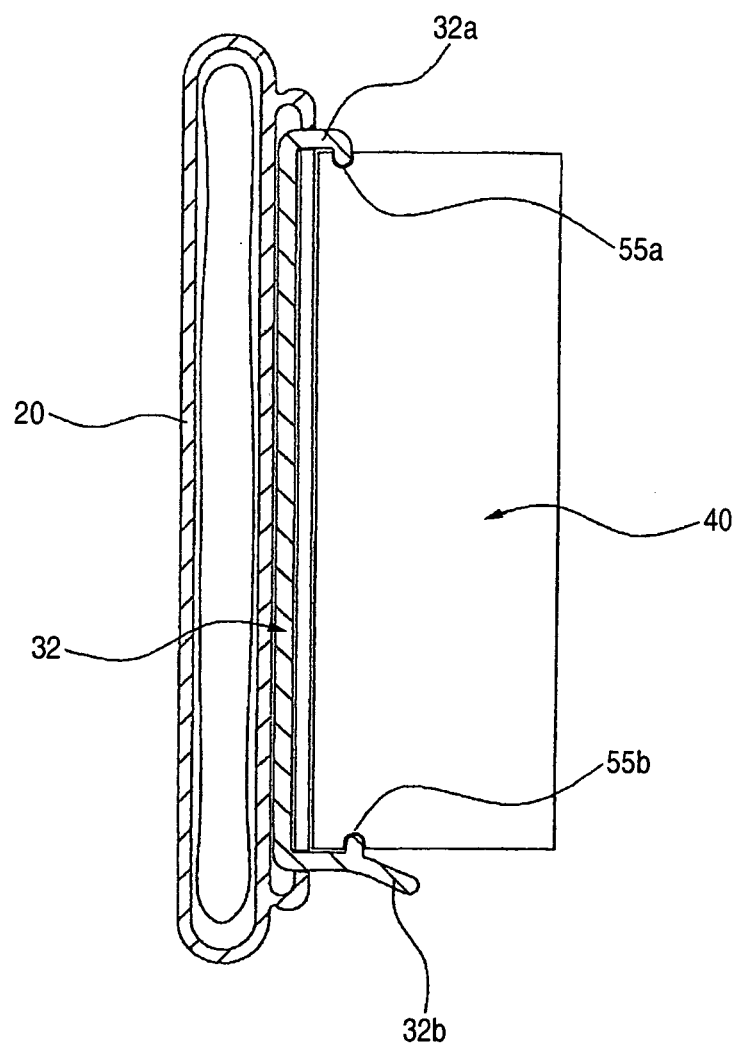
FIG. 10 is a vertical section view showing an engagement structure between the vital sign telemeter and the retainer.
Figure 11:
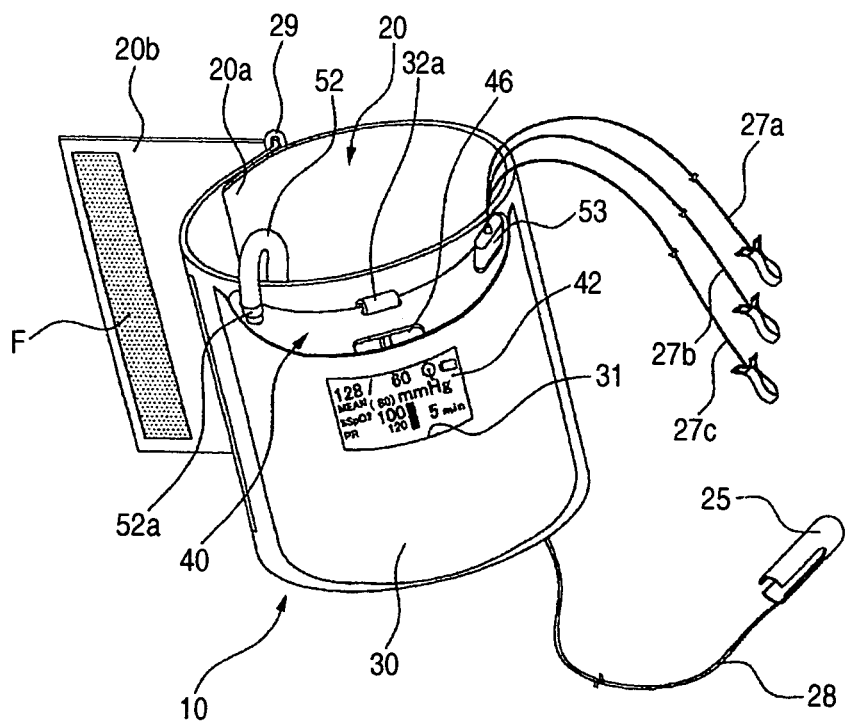
FIG. 11 is a perspective view of the vital sign telemeter and the cuff showing a state after the vital sign telemeter is attached on the cuff.

Next, how to attach the main body 40 of the vital sign telemeter 10 onto the cuff 20 will be explained with reference to FIGS. 9 and 11. In this embodiment, the back face of the main body 40 formed into a curved shape is butted against the retainer 32 which is attached to the cuff 20 shown in hitherto described FIGS. 5 and 6, and the engagement sections 32a, 32b of the retainer 32 are engaged with the slits 55a, 55b (see FIGS. 4 and 5) provided on the top face and the bottom face of the main body 40 (see FIGS. 9 and 10). Thereafter, the front face of the main body 40 is covered with the sheet cover 30 in a surrounding manner, and fixed by the hook-and-loop fasteners F as required. FIG. 11, shows a state that the assembly of the vital sign telemeter 10 is completed.

Figure 12A:
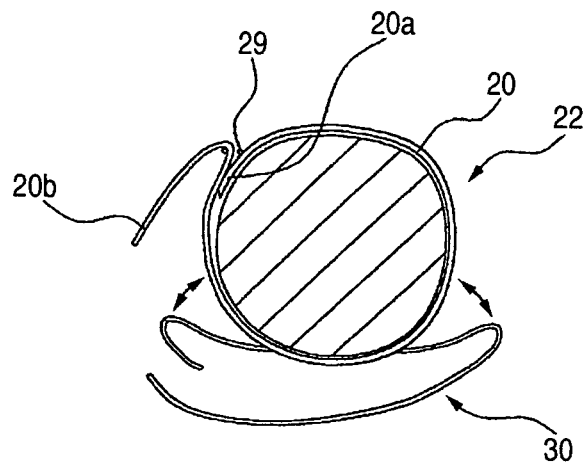
FIG. 12A is a schematic view showing an applied state of the cuff to a patient a thin arm.
Figure 12B:
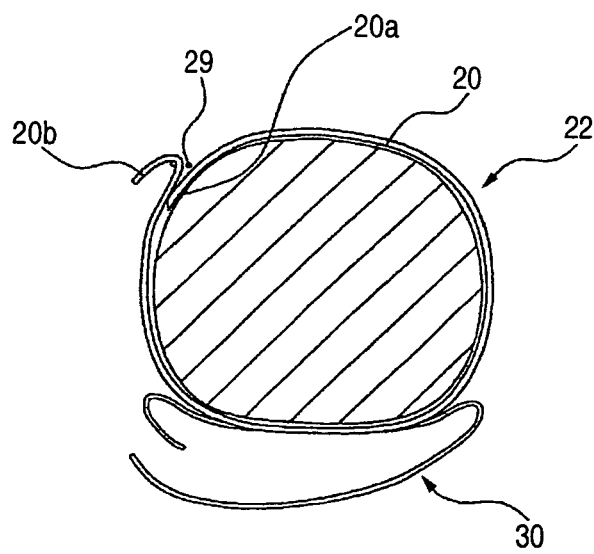
FIG. 12B is a schematic view showing an applied state of the cuff to a patient having a thick arm.

FIG. 12A shows an applied state of the cuff 20 attached to a patient having a thin arm. FIG. 12B shows an applied state of the cuff 20 attached to a patient having a thick arm. As shown in the drawings, the cuff 20 can be applied in such a manner as to fit an arm of each patient in terms of size, by adjusting the turning-up length of the other end 20b of the cuff, which is the length to be turned up after passing through the size adjustment ring 29.

Figure 13:
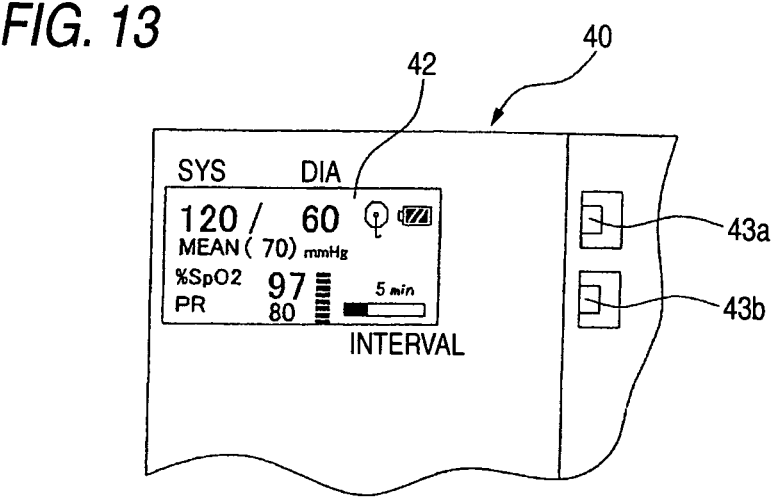
FIG. 13 is an enlarged view of a display of the vital sign telemeter.

FIG. 13 shows an example display of the main body 40 of the vital sign telemeter 10. More specifically, the display 42 can display a systolic blood pressure "SYS 120 mmHg", a diastolic blood pressure "DIA 60 mmHg", a mean blood pressure "MEAN (70) mmHg", an SpO2 value "% SpO2 97", a pulse rate "PR 80", measurement interval "5 min", and others, such as a bar graph indicating the pulse wave, marks for indicating the electrode removal, the residual amount of the battery, and the error condition or the like.

Meanwhile, the NIBP measurement can be started and stopped arbitrarily, by operating the measurement start/stop switch 43a in compliance with contents appearing on the display 42. In addition, intervals of the NIBP measurement can be set to a desired value, by operating the measurement interval setting switch 43b in sequence of; e.g., "manual-5 minutes-10 minutes-30 minutes-60 minutes, etc.," to thus select any one.

Figure 14:
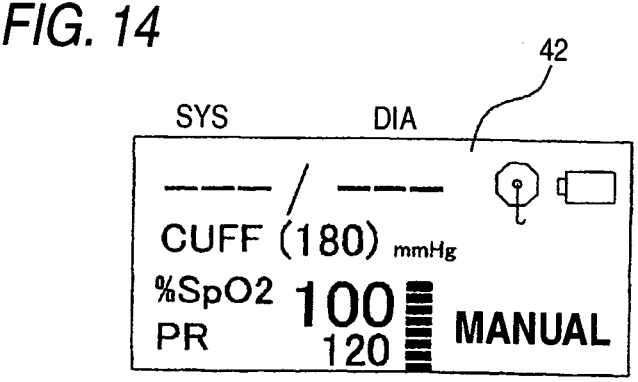
FIGS. 14 and 15 are enlarged views showing examples of contents displayed in the display.
Figure 15:
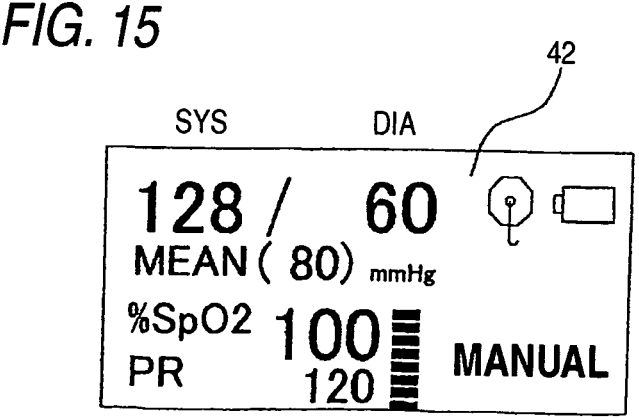

FIG. 14 shows an example display of the display 42 in a case where the cuff 20 is inflated manually. FIG. 15 shows an example of the display 42 in a case where the measurement is completed. More specifically, FIG. 14 shows a case where a cuff pressure "CUFF (180) mmHg" is displayed; and FIG. 15 shows a case where a systolic blood pressure "SYS 128 mmHg", a diastolic blood pressure "DIA 60 mmHg", and a mean blood pressure "MEAN (80) mmHg" are respectively displayed.

Figure 16:
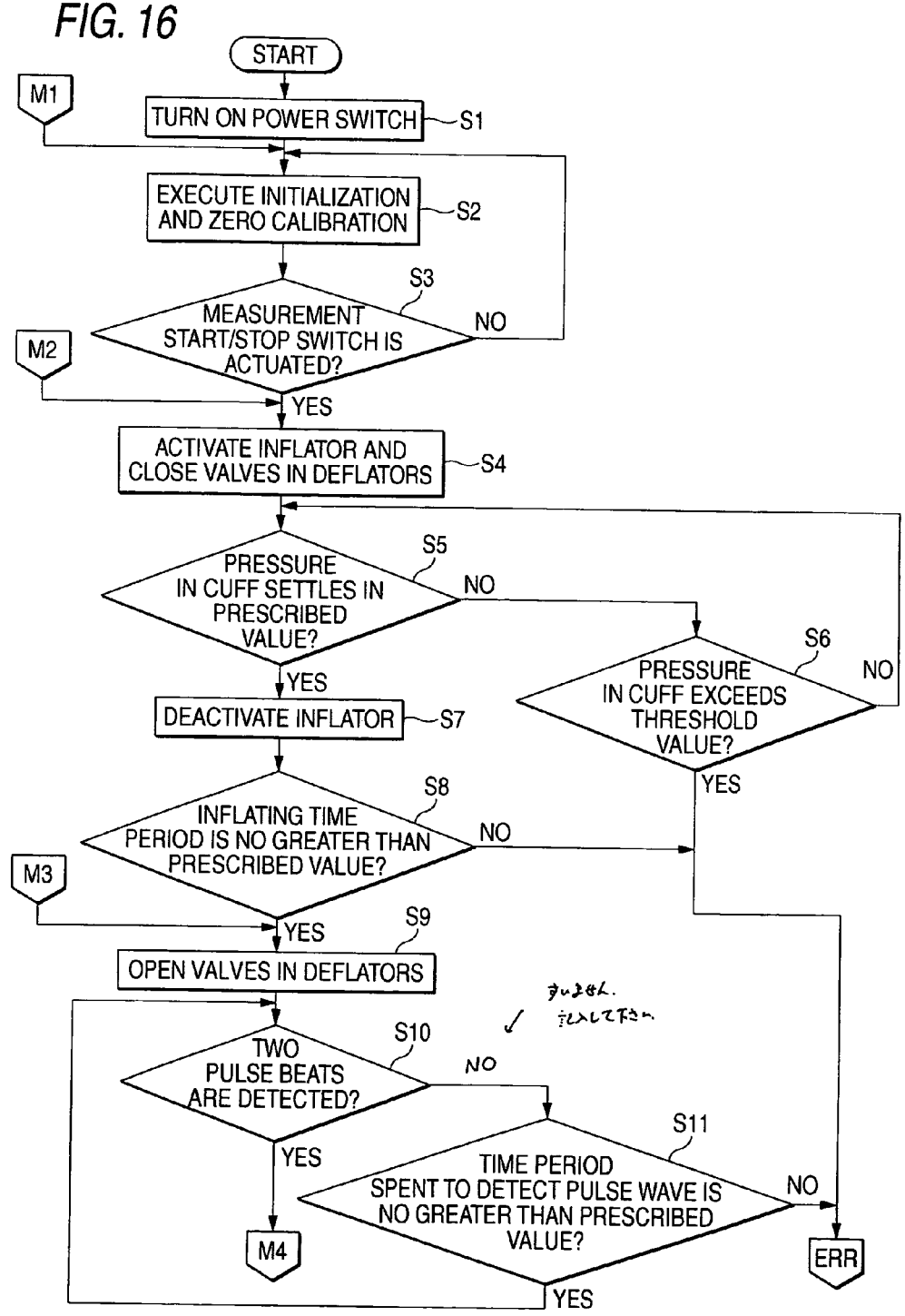
FIG. 16 is a flowchart of a measuring operation program for vital signals executed by the vital sign telemeter.
Figure 16:
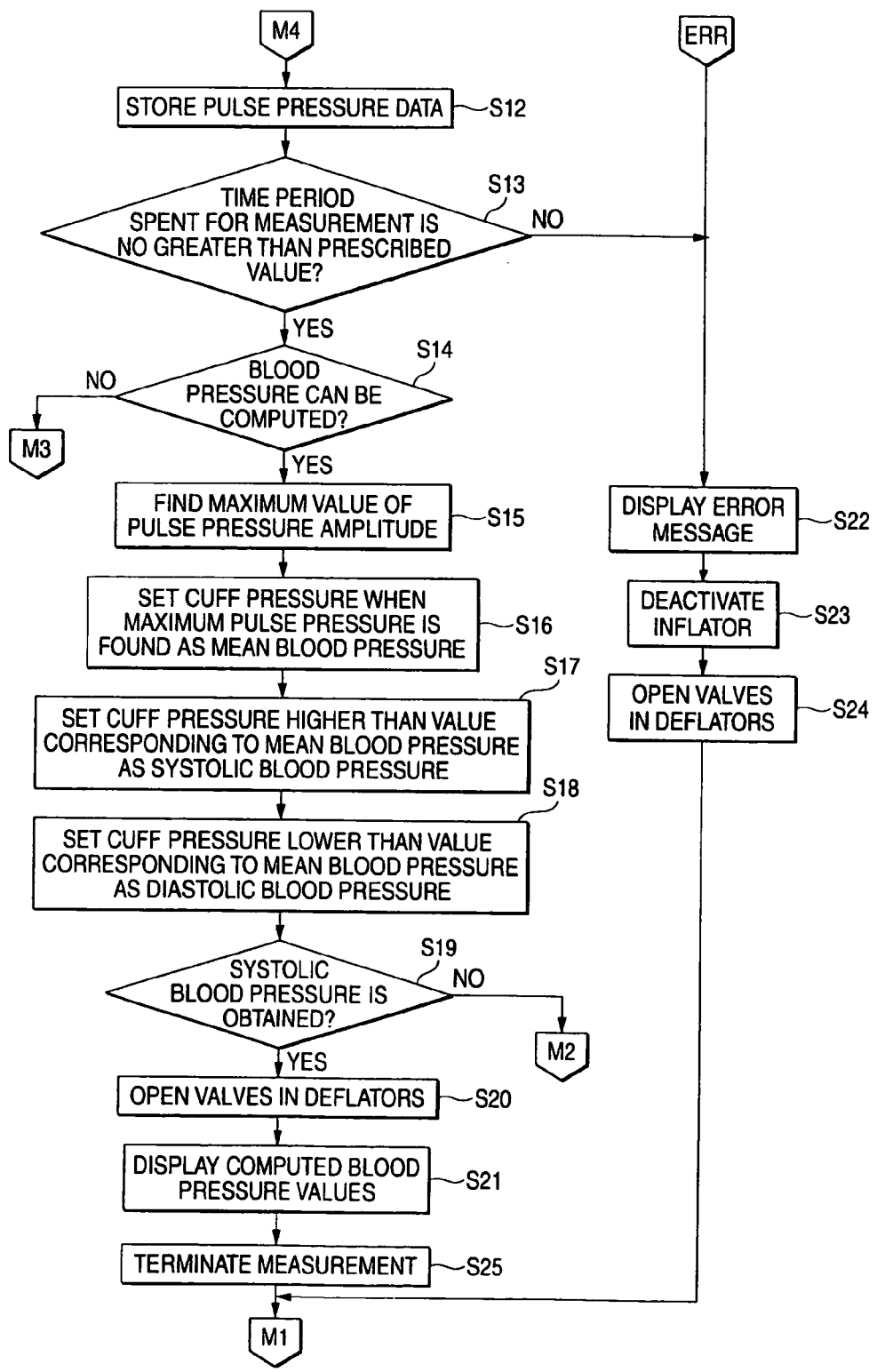

FIG. 16 is a flowchart of measuring operation program for performing measurement of respective vital signals with use of the vital sign telemeter 10 attached to a patient. Hereinafter, operations of a measurement program will be described in connection with the system configuration of the vital sign telemeter 10 shown in FIG. 2.

For starting measurement of the respective vital signals of a patient the power switch 46 of the vital sign telemeter 10 is turned on (step S1). Subsequently, initialization and zero-calibration of NIBP measurement are performed (step S2), and the measurement start/stop switch 43a is operated. At this time, when measurement start by the measurement start/stop switch 43a is determined (step S3), a pump action of the inflator 70 for supplying air pressure to the cuff 20 is started, and solenoid valves of the deflators 71, 73 are closed (step S4). Thereafter, whether or not the pressure of the cuff 20 has settled in a prescribed pressure is determined (step-5). When the pressure has settled in the prescribed pressure, pump action of the inflator 70 is stopped (step S7). When the pressure has not settled in the prescribed pressure, whether or not the pressure exceeds a threshold pressure which has been set in advance is determined (step S6). When the pressure has not exceeded the threshold pressure, reach for the prescribed pressure is rechecked; and when the pressure has exceeded the same, error processing ERR is executed.

When the pressure of the cuff 20 reaches the prescribed pressure and the pump action is stopped, whether or not the inflating time period is no greater than a prescribed value is determined (step S8). When the inflating time period is no greater than the prescribed value, the solenoid valves of the deflators 71, 73 are opened for a prescribed time period, thereby exhausting air in the cuff 20 (step S9). When the inflating time period exceeds the prescribed value, the error processing ERR is executed.

Next, whether or not two pulse beats have been detected is determined (step S10). When detected, pulse pressure data detected at this time is stored (step S12). When the two pulse beats have not been detected, whether or not the time period spent for the detection is no greater than a prescribed value for pulse wave detection is determined (step S11). When the time period is no greater than the prescribed value, the pulse is rechecked; and when the time period has exceeded the prescribed value, the error processing ERR is executed.

When the pulse pressure data is stored in step S12, whether or not the time period spent for the measurement is no greater than a prescribed value is determined (step S13). When the time period is no greater than the prescribed value, whether or not blood pressure can be computed is determined (step S14). When it is determined that the blood pressure can be computed, the maximum value of the pulse pressure amplitude is obtained (step S15).

When the time period spent for the measurement exceeds the prescribed value, the error processing ERR is executed; and when it is determined that the blood pressure cannot be computed, the routine is returned to step S9, thereby repeating the process to step S14.

Here, a pressure value of the cuff 20 when the pulse pressure has the maximum value is set as a mean blood pressure (step S16). A pressure value of the cuff 20 higher than the value corresponding to the mean blood pressure when the pulse pressure has a half value of the maximum value is set as a systolic blood pressure (step S17). A pressure value of the cuff 20 lower than the value corresponding to the mean blood pressure when the pulse pressure has a half value of the maximum value is set as a diastolic blood pressure (step S18). Thereafter, whether or not the systolic blood pressure has been computed is determined (step S19). When computed, the solenoid valves of the deflators 71, 73 are opened (step S20); and computation result of the blood pressure values is displayed on the display 42 (step S21), thereby terminating a single measurement. When the systolic blood pressure has failed in computation, the routine is returned to the step S4, thereby repeating the processing to step S19.

The error processing ERR is executed such that description of the error is displayed on the display 42 (step S22); pump action of the inflator 70 is stopped (step S23); and the solenoid valves of the deflators 71, 73 are opened (step S24), thereby terminating the measurement (step S25). Subsequent blood pressure measurement is performed by repeating the routine from step S2 to step S25 after a prescribed interval.

Figure 17:
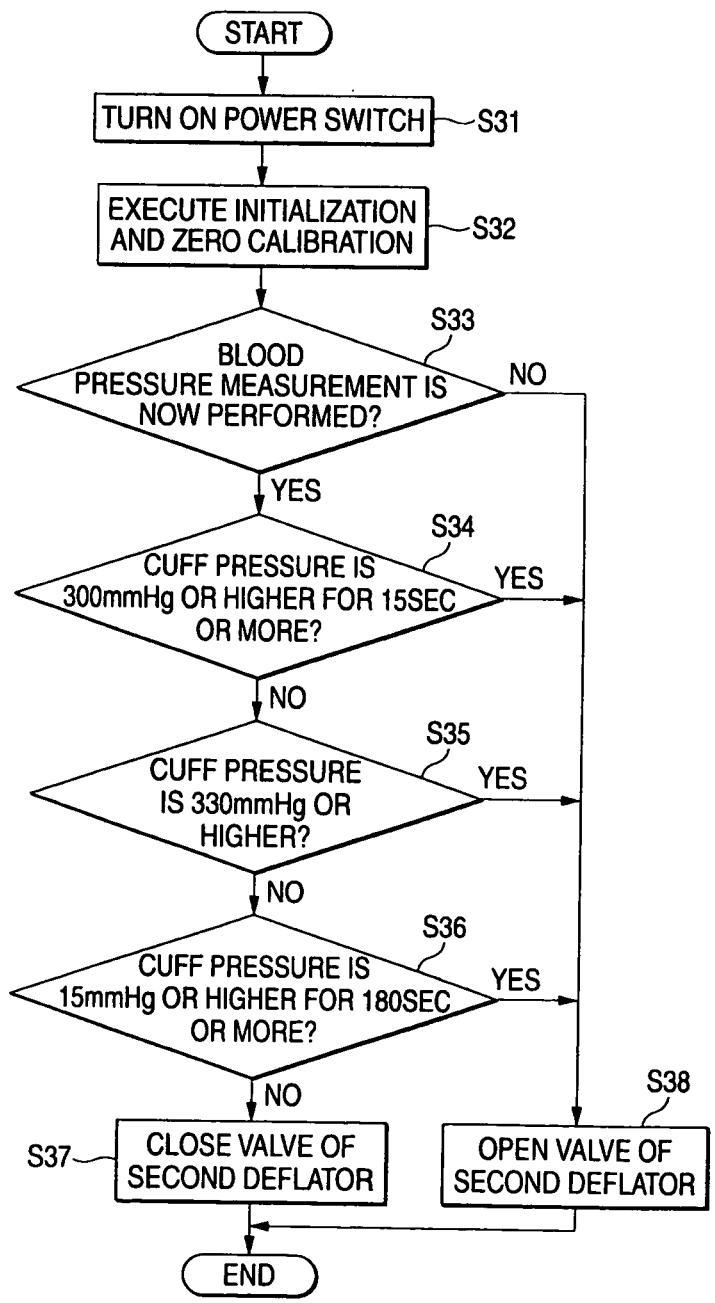
FIG. 17 is a flowchart showing of a safety control action program executed by the vital sign telemeter.

FIG. 17 shows a flowchart of a safety control action program executed when the vital sign telemeter 10 attached to a patient to measure NIBP falls into a single fault condition as specified in IEC 60601-2-30 Ed. 2.0:1999 (en). Concretely, the single fault condition is defined as any single defect which: a) results in a failure of an adjuster for pressure of the cuff; b) prevents deflation of the cuff within the prescribed time period; and c) results in a failure of the timing for inflating the cuff.

Hereinafter, details of the safety control action program will be described on the basis of a relation with the system configuration of the vital sign telemeter 10 shown in FIG. 2.

In FIG. 17, for starting measurement of the respective vital signals of a patient by the vital sign telemeter 10, the power switch 46 is turned on (step S31). Subsequently, initialization and zero calibration of NIBP measurement is performed (step S32). Thereafter, whether or not the measurement start/stop switch 43*a* is operated, or whether or not the blood pressure is being measured with a prescribed measurement interval is determined (step S33). When the blood pressure is being measured, the second pressure detector 74 determines whether or not a state where the cuff pressure is 300 mmHg or higher is continued for 15 seconds or longer is detected (step S34). Incidentally, when the blood pressure is not being measured, the solenoid valve of the second deflator 73 is opened (step S38), thereby terminating the measurement. At this time, when the above state is detected at step S34, in order to avert a danger, the solenoid valve of the second deflator 73 is opened (step S38), thereby terminating the measurement immediately.

When the above state is not detected at step S34, the second pressure detector 74 determines whether or not the cuff pressure has reached 330 mmHg or higher is detected (step S35). When the above state is detected at step S35, in order to avert a danger, the solenoid valve of the second deflator 73 is opened (step S38), thereby terminating the measurement immediately.

On the other hand, when the above state is not detected at step S35, the second pressure detector 74 determines whether or not a state where the cuff pressure is 15 mmHg or higher continues for 180 seconds or longer is detected (step S36). At this time, when the above state is detected at step S36, in order to avert a danger, the solenoid valve of the second deflator 73 is opened (step S38), thereby terminating the measurement. When the above state is not detected at step S36, the blood pressure measurement is performed by the second pressure detector 74 while closing the solenoid valve of the second deflator 73 (step S37). In this case, the main controller 60 drives the inflator 70 to measure blood pressure with the first pressure detector 72. At the same time, the main controller 60 sends a signal indicating that the blood pressure measurement is now performed to the auxiliary controller 64, thereby the auxiliary controller 64 recognizes that the blood pressure measurement is executed by the main controller 60.

Figure 18A:
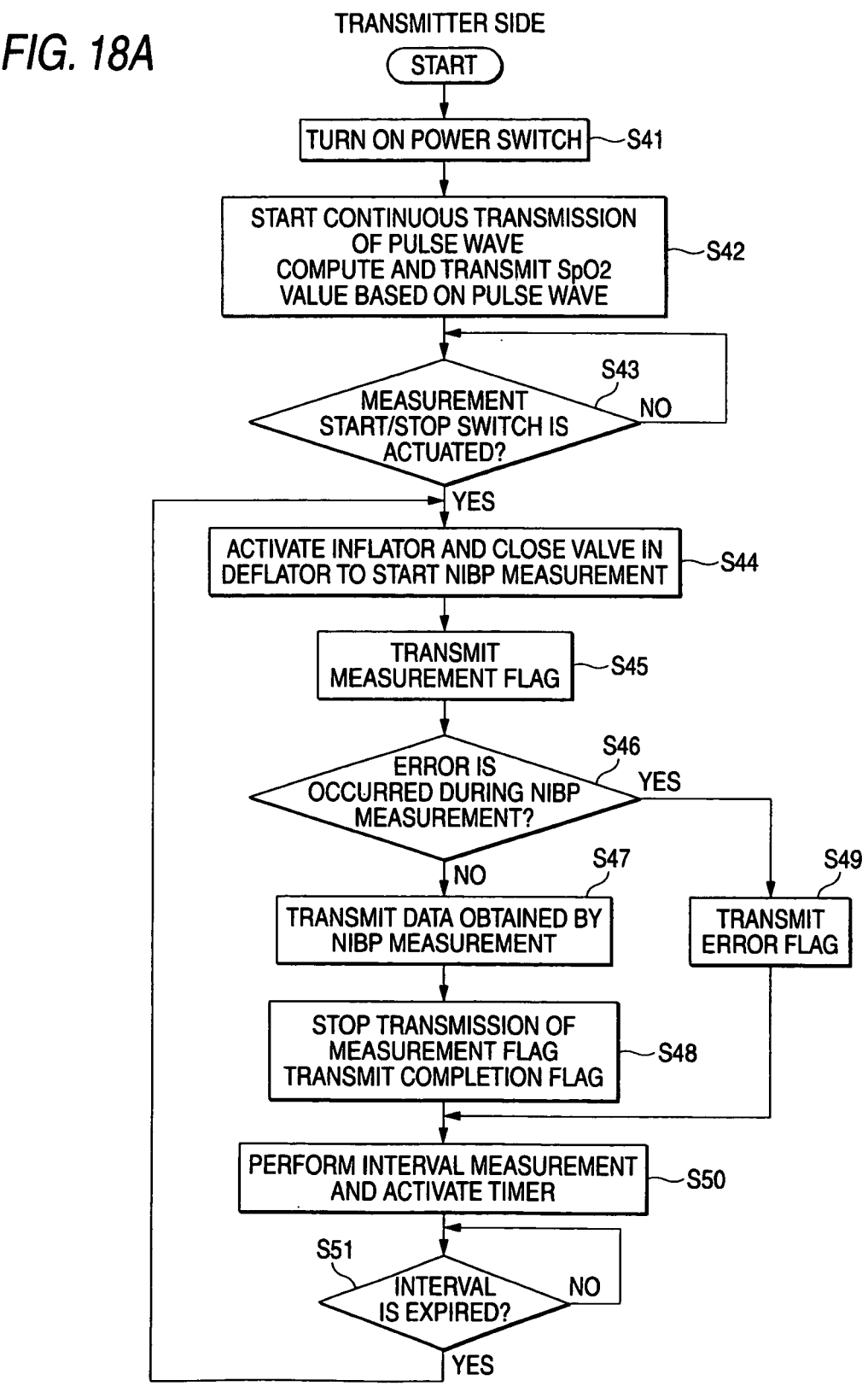

FIGS. 18A and 18B are flowcharts of a communication control program for controlling transmission of vital signals measured by attaching the vital sign telemeter 10 to a patient; and for controlling receipt of the vital signals at a remote location. Hereinafter, details of the communication control program will be described on the basis of a relation with the system configuration of the vital sign telemeter 10 shown in FIG. 2.

For starting transmission control in the transmission controller 68, as shown in FIG. 18A, the power switch 46 is turned on (step S41). Electrocardiogram waveform data, pulse waveform data, respiratory waveform data obtained by the electrocardiogram and respiration detector 24, and SpO2 data obtained by the SpO2 detector 26 are then respectively transmitted to a receiver (step S42). Subsequently, when it is detected measurement start by the actuation of the measurement start/stop switch 43*a* (step S43), a pump action of an inflator 70 for supplying air to the cuff 20 is started, and solenoid valves of the deflators 71, 73 are closed, whereby NIBP measurement is started (step S44). Upon start of the NIBP measurement, a measurement flag indicating that the blood pressure is being measured is transmitted to the receiver (step S45).

During the period during which blood pressure is being measured, whether or not an error has been found is determined (step S46). When no error has been found, data obtained by the NIBP measurement are transmitted to the receiver (step S47). Thereafter, transmission of the measurement flag is stopped, and a completion flag indicating that the blood pressure measurement is completed is transmitted to the receiver (step S48). In addition, when an error has been found during the period during which blood pressure is being measured, an error flag is transmitted to the receiver (step S49).

By the way, since the blood flow is stopped by the inflated cuff 20, the measured SpO2 value may be unreliable during the NIBP measurement. Accordingly, in this embodiment, the main controller 60 causes the transmission controller 68 to transmit information indicating that the measured SpO2 value is unreliable while the NIBP measurement is performed. In addition, the measured SpO2 value may be unreliable until the blood flow stopped by the inflated cuff restores to the normal condition after the deflation of the cuff. Accordingly, in this embodiment, the main controller 60 determines whether the SpO2 value is reliable or not after the NIBP measurement is finished. For example, it is judged whether a prescribed time period is elapsed after the completion of the NIBP measurement. When it is determined that the measured SpO2 value is reliable, the main controller 60 causes the transmission controller 68 to transmit information indicating that the measured SpO2 value is reliable.

Thereafter, a timer is activated to count a prescribed measurement interval (e.g., 5 minutes) (step S50). When the prescribed interval is expired, the routine is returned to step S44, thereby repeating the control actions to step S50.

Figure 19:
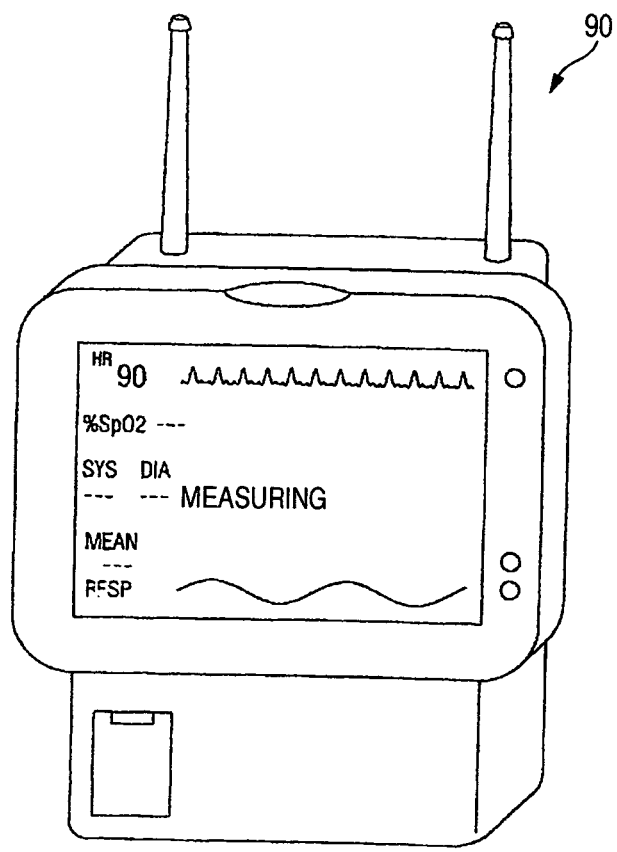
FIG. 19 is a perspective view of the receiver.

On the other hand, for starting receiving control with the receiver, the power switch is turned on (step S61) as shown in FIG. 18B. Upon the activation, whether or not the respective data from the transmission controller 68 have been received is determined (step S62). When the transmission data have been received, the respective received data are displayed (step S63). Subsequently, when the transmission data have failed in receiving or after the respective received data have been displayed respectively, whether or not the measurement flag transmitted from the transmission controller 68 has been received is determined (step S64). When the measurement flag has been received, display indicating that blood pressure is being measured is performed, and display of SpO2 value is erased, whereby an alarm about receiving processing of the SpO2 value is cancelled. FIG. 19 shows a monitor screen of a vital sign data receiver 90 as a display example in the receiver.

Meanwhile, the receiver 90 determines whether the information indicating that the measured SpO2 value is unreliable is received from the transmission controller 68. When it is determined that the information is received, the receiver 90 holds the measured SpO2 value (e.g., 97%) at the moment that the information is received.

In addition, an indication that the measured SpO2 value is unreliable due to the NIBP measurement is performed on the display of the receiver 90. For example, the numerical value which has been displayed is deleted; a symbol "-" or the like is displayed instead of the numerical value which has been displayed; the displayed numerical value is caused to blink or the color of the displayed numerical value is change with a message that the displayed SpO2 value is unreliable. Namely, even if the measured SpO2 value or the measured pulse rate decrease, the receiver 90 judges that such changes are caused by the NIBP measurement, and will not generate an alarm or the like indicating the serious decrease of the SpO2 value.

When the receiver 90 receives the information indicating that the measured SpO2 value is reliable, the holding of the measured SpO2 value is canceled and the displayed numerical value is updated by the latest measured SpO2 value. The display of the measured SpO2 value is continued in a real time manner after then.

There may be configured such that the holding of the measured SpO2 value is effected when the receiver 90 receives a flag indicating the initiation of the NIBP measurement.

Thereafter, whether NIBP measurement data from the transmission controller 68 have been received or not, or whether an error flag has been received during the NIBP measurement is determined (step S67). When the NIBP measurement data have been received, the received blood pressure value is displayed (step S68). When the error flag has been received, display indicating the NIBP measurement fault is performed (step S69). Subsequently, whether or not the completion flag from the transmission controller 68 has been received is determined (step S70). When the completion flag has been received, an SpO2 value is displayed, and an alarm indicating receiving processing of SpO2 value is enabled (step S71). The routine is returned to step S62, thereby repeating the control actions to step S71.

Figure 20:
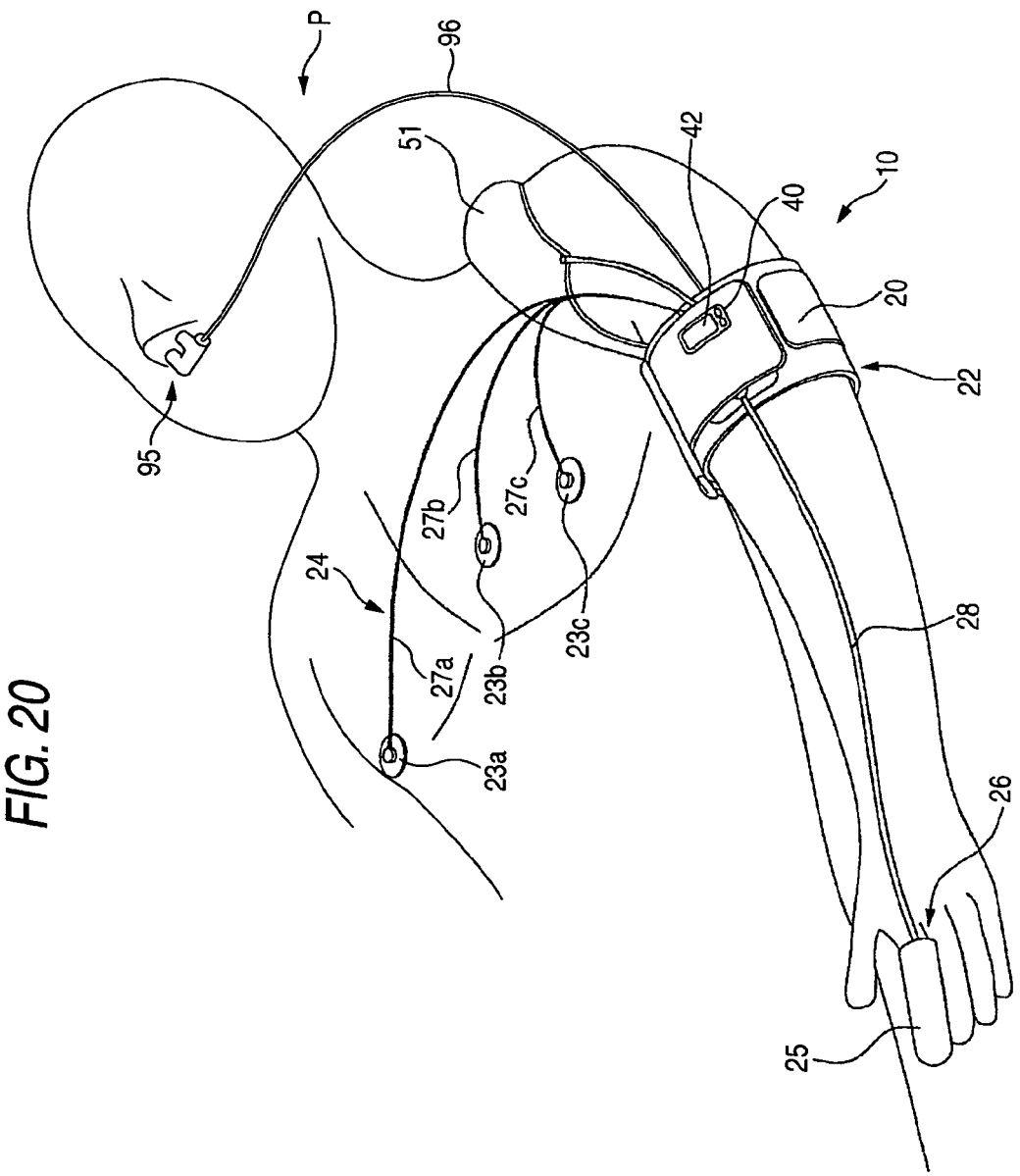
FIG. 20 is a perspective view of a vital sign telemeter according to a second embodiment of the invention, showing a state that the telemeter is attached onto a patient's body.

The preferred embodiment of the invention has hitherto been described. However, it should be understood that the invention is not limited thereto, and may variously be modified, altered, and changed within the scope of the invention. For example, the measured parameter may include a concentration of carbon dioxide in gas expired through nostrils, electroencephalogram and electromyogram of the subject. In a case where the concentration of carbon dioxide in gas expired through nostrils is measured, as shown in FIG. 20, a carbon dioxide sensor 95 is placed below the nostrils of the patient P and signals indicating the concentration of carbon dioxide are transmitted to the vital sign telemeter 10 via a lead wire 96 connecting the main body 40 and the carbon dioxide sensor 95.

What is claimed is:

1. A vital sign telemeter comprising:
a first detector comprising a cuff adapted to be placed on a first part of a subject to detect non-invasive blood pressure of the subject, and connected to a cuff hose;
at least one second detector adapted to be placed on a second part of the subject to detect at least one additional vital sign of the subject, and connected to a lead wire;
a single main body including a first connector to which the cuff hose is detachably connected, and a second connector to which the lead wire is detachably connected;
a display provided in the main body, and operable to display the non-invasive blood pressure and the at least one additional vital sign;
a transmitter provided in the main body, and operable to transmit the non-invasive blood pressure and the at least one additional vital sign to a receiver placed in a remote location;
a retainer configured to be attached to a third part of the subject to retain the main body; and
a cover configured to surround the main body, and formed with a window adapted to expose the display provided in the main body when the main body is surrounded by the cover,
wherein the first connector and the second connector of the main body are exposed to outside from the cover when the main body is surrounded by the cover.

2. The vital sign telemeter according to claim 1, wherein the retainer is wound around the third part of the subject to retain the main body.

3. The vital sign telemeter according to claim 2, wherein the third part of the subject is one of a shoulder, a waist and an arm of the subject.

4. The vital sign telemeter according to claim 1, wherein the at least one second detector includes at least one of:
a plurality of electrodes adapted to be attached on at least one of a chest and a limb of the subject to detect one of electrocardiogram and respiration of the subject;
a sensor adapted to be attached on a finger of the subject to detect oxygen saturation in blood of the subject; and
a sensor adapted to be attached on a face of the subject to detect a concentration of carbon dioxide in gas expired through nostrils of the subject.

5. The vital telemeter according to claim 4, further comprising:
a controller configured to set an interval between periodic activation of the first detector, and configured to determine a pulse rate based on a detected pulse wave,
wherein the first detector is operable to detect the pulse wave, and
wherein the display is so configured as to simultaneously display the non-invasive blood pressure, the at least one additional vital sign, the pulse rate, the pulse wave, and the interval between periodic activation of the first detector.

6. A telemeting method, comprising steps of:
providing a first detector comprising a cuff adapted to be placed on an upper arm of a subject;
providing at least one second detector including a sensor adapted to be attached on a finger of the subject to detect oxygen saturation in blood of the subject;
connecting the first detector and the at least one second detector to a single main body which is detachably provided on the cuff;
detecting non-invasive blood pressure of the subject through the first detector;
detecting the oxygen saturation in blood of the subject through the second detector;
displaying the non-invasive blood pressure and the oxygen saturation in blood of the subject on a display provided on the main body, as measurement data;
transmitting the measurement data to a receiver placed in a remote location; and
transmitting information indicating that the measurement data for the oxygen saturation is unreliable at least while the first detector detects the non-invasive blood pressure.

7. A telemeting system, comprising:
a first detector, comprising a cuff adapted to be placed on an upper arm of a subject to detect non-invasive blood pressure of the subject;
at least one a second detector, including a sensor adapted to be placed on a finger of the subject to detect oxygen saturation in blood of the subject;
a single main body, detachably provided on the cuff while being connected with the first detector and the second detector;
a receiver, placed in a remote location from the main body and provided with an indicator; and
a transmitter, provided in the main body and operable to transmit the non-invasive blood pressure and the oxygen saturation in blood as measurement data to the receiver, wherein:
the transmitter transmits information indicating that the measurement data for the oxygen saturation is unreliable at least while the first detector detects the non-invasive blood pressure, to the receiver; and the indicator indicates that the measurement data for the oxygen saturation received from the transmitter is unreliable when the receiver receives the information.

\* \* \* \* \*